(12) United States Patent
Weiss et al.

(10) Patent No.: US 9,662,281 B2
(45) Date of Patent: May 30, 2017

(54) SOLID LIPID NANOPARTICLES (II)

(71) Applicant: DSM IP ASSETS B.V., Heerlen (NL)

(72) Inventors: Jochen Weiss, Basel (CH); Christiane Maier, Basel (CH); Anne Kessler, Basel (CH); Concetta Tedeschi, Basel (CH); Bruno Leuenberger, Basel (CH); Markus Nowotny, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/774,855

(22) PCT Filed: Mar. 14, 2014

(86) PCT No.: PCT/EP2014/055093
§ 371 (c)(1),
(2) Date: Sep. 11, 2015

(87) PCT Pub. No.: WO2014/140268
PCT Pub. Date: Sep. 18, 2014

(65) Prior Publication Data
US 2016/0030305 A1  Feb. 4, 2016

(30) Foreign Application Priority Data

Mar. 15, 2013 (EP) .................... 13159488

(51) Int. Cl.
| | | |
|---|---|---|
| A61K 8/02 | (2006.01) | |
| A61K 8/06 | (2006.01) | |
| A61K 47/14 | (2017.01) | |
| A61K 9/10 | (2006.01) | |
| A61K 9/51 | (2006.01) | |
| A61K 8/37 | (2006.01) | |
| A61Q 19/00 | (2006.01) | |
| A61K 8/55 | (2006.01) | |
| A23K 40/30 | (2016.01) | |
| A23P 10/35 | (2016.01) | |
| A23L 27/00 | (2016.01) | |

(52) U.S. Cl.
CPC ............... *A61K 8/06* (2013.01); *A23K 40/30* (2016.05); *A23L 27/72* (2016.08); *A23P 10/35* (2016.08); *A61K 8/0241* (2013.01); *A61K 8/37* (2013.01); *A61K 8/375* (2013.01); *A61K 8/553* (2013.01); *A61K 9/10* (2013.01); *A61K 9/5176* (2013.01); *A61K 47/14* (2013.01); *A61Q 19/00* (2013.01); *A23V 2002/00* (2013.01); *A61K 2800/10* (2013.01); *A61K 2800/412* (2013.01); *A61K 2800/652* (2013.01)

(58) Field of Classification Search
USPC ......................................................... 424/401
See application file for complete search history.

(56) References Cited

U.S. PATENT DOCUMENTS

| | | | |
|---|---|---|---|
| 8,728,527 B2 * | 5/2014 | Singh ...................... | A61K 9/10 424/489 |
| 9,180,210 B2 * | 11/2015 | Texier-Nogues .... | A61K 9/0019 |
| 2009/0238878 A1 * | 9/2009 | Singh ...................... | A61K 9/10 424/489 |
| 2013/0017239 A1 * | 1/2013 | Viladot Petit ........ | A61K 8/0283 424/401 |

FOREIGN PATENT DOCUMENTS

| | | |
|---|---|---|
| CA | 2 834 921 | 10/2012 |
| CN | 101 606 907 | 12/2009 |
| CN | 102 670 484 | 9/2012 |
| EP | 2 481 396 | 8/2012 |

OTHER PUBLICATIONS

International Search Report for PCT/EP2014/055093 mailed Apr. 29, 2014, three (3) pages.

* cited by examiner

*Primary Examiner* — Rei-Tsang Shiao
(74) *Attorney, Agent, or Firm* — Nixon & Vanderhye P.C.

(57) ABSTRACT

The present invention relates to new (foodgrade) solid lipid nanoparticles, as well as the production of such solid lipid nanoparticles and the use of them.

10 Claims, No Drawings

SOLID LIPID NANOPARTICLES (II)

This application is the U.S. national phase of International Application No. PCT/EP2014/055093 filed 14 Mar. 2014 which designated the U.S. and claims priority to EP Patent Application No. 13159488.9 filed 15 Mar. 2013, the entire contents of each of which are hereby incorporated by reference.

The present invention relates to new (foodgrade) solid lipid nanoparticles, as well as the production of such solid lipid nanoparticles and the use of them.

Solid lipid nanoparticles (SLNs) are for example used as a novel approach for oral as well as for parental lipophilic or amphiphilic active ingredients delivery. Today the most common way for such delivery are emulsions.

SLN are suitable for such a use due to several important advantages such as
(i) incorporation of lipophilic as well as amphiphilic active ingredients, and
(ii) no biotoxicity, and
(iii) avoidance of organic solvents, and
(iv) possibility of controlled active ingredients release, and
(v) excellent stability (mechanical and chemical), and
(vi) usable for spray-drying, and
(vii) good optical properties (allows the production of non-turbid formulations), and
(viii) sterilisable.

SLNs have a (more or less) spherical shape with a diameter of 10-1000 nm. In case non-turbid formulation are to be produced, then the diameter of the SLNs should be between 50-300 nm.

SLNs possess a solid lipid core which is stabilized by emulsifiers.

SLNs are known from the prior art such as Mehnert et al., Adv. Drug Del. Rev. 47 (2001), 165-196.

The lipid phase (lipid core) of the SLN is in a solid state (aka crystallized). This phase may comprise lipophilic and/or amphiphilic active ingredients (such as antimicrobial, antioxidants, polyphenols, vitamins, poly unsaturated fatty acids (PUFAs), dyestuffs, etc), which are (if they are included in the solid state) protected from degradation.

This is a very important further advantage which allows to prolonging the shelf life of lipophilic or amphiphilic active ingredients in a sophisticated way.

Crystallized lipids can form usually three different kinds of crystals:
$\alpha$, $\beta'$, and $\beta$ crystals.

The $\alpha$-crystal chains have hexagonal arrangement, with the shortest spacing line in X-ray diffraction pattern. Furthermore, this crystal type has the least densely packed lipid structure and it melts at temperatures below that of the other crystals.

The $\beta'$-crystals are the transition form between $\alpha$- and $\beta$-crystals, and they are orthorhombic. They are more ordered than $\alpha$-crystals and melt at higher temperatures.

The $\beta$-crystals are packed in triclinic arrangement and have highly ordered platelet-like structures. They are the most stable form, and therefore they melt at the highest temperature. Due to kinetic reasons the crystals rearrange themselves from less ordered $\alpha$-crystals to highly ordered $\beta$-crystals implying a shape change from spherical to plated shaped particles (Bunjes, Steiniger, & Richter, 2007). From this it follows, that the oil-water surface area increases leading to aggregation and gel formation of hydrophobic patches.

But in order to include a bioactive ingredient into the lipid core of the SLN, without incurring the above mentioned phase separation the unstable $\alpha$ and/or $\beta'$-crystal structure is preferred.

The goal of the present invention is to find a way to provide SLN with a $\alpha$ and/or $\beta'$-crystal structure which is stable and therefore does not polymorph into the $\beta$ crystal structure. The SLN must be (storage) stable for weeks.

Surprisingly, it was found that when a specific emulsifier (which is at least one citric acid ester) was used, then a stable SLN wherein the solid lipid has a $\alpha$ and/or $\beta'$-crystal structure is obtained.

Therefore the present invention relates to solid lipid nanoparticles (I) comprising
(a) a core comprising
(i) a lipid phase in a solid state, and
(ii) optionally at least one lipophilic and/or amphiphilic active ingredient, and
(b) an emulsifier system comprising
(i) at least one emulsifier
characterised in
that the emulsifier system comprises at least one citric acid ester (preferably at least one citric acid ester of mono- and di-glycerides).

Furthermore it is preferred that the emulsifier system of the SLN has a crystallization point which is lower than the crystallization point of the core of the SLN. That means that the emulsifier system should crystallize before the core crystallizes.

Therefore the present invention also relates to solid lipid nanoparticles (II), which are solid lipid nanoparticles (I), wherein the emulsifier system has a crystallization point which is lower than the crystallization point of the core.

The lipid phase can be any oil (mixture of oils), which is solid at the storage temperature of the SLN. Suitable oils are for example triglycerides, partial glycerides, fatty acids, steroids and waxes.

Therefore the present invention also relates to solid lipid nanoparticles (III), which are solid lipid nanoparticles (I) or (II), wherein the lipid phase is an oil (mixture of oils), which is solid at the storage temperature of the SLN. Suitable oils are for example triglycerides, partial glycerides, fatty acids, steroids and waxes.

Therefore the present invention also relates to solid lipid nanoparticles (III'), which are solid lipid nanoparticles (I), (II) or (III), wherein the lipid phase is an oil (mixture of oils) chosen from the group consisting of triglycerides, partial glycerides, fatty acids, steroids and waxes.

The lipophilic and/or amphiphilic active ingredient can be for example an antimicrobial, an antioxidant, a polyphenol, a vitamin, a PUFA or a dyestuff, as well as mixtures of such ingredients.

Therefore the present invention also relates to solid lipid nanoparticles (IV), which are solid lipid nanoparticles (I), (II), (III) or (III'), wherein the lipophilic and/or amphiphilic active ingredient is chosen from the group consisting of antimicrobial, an antioxidant, a polyphenol, a vitamin, a PUFA or a dyestuff, as well as mixtures of such ingredients.

The (specific) emulsifier which is used in the embodiment of the present invention is at least one citric acid ester. Preferably it is at least one citric acid ester of mono- and di-glycerides. More preferably at least one citric acid ester of mono and diglycerides of fatty acids (E472c). The E numbers (i.e. E472c) are codes for chemicals which can be used as food additives for use within the European Union and Switzerland (the "E" stands for "Europe").

Therefore the present invention also relates to solid lipid nanoparticles (V), which are solid lipid nanoparticles (I), (II), (III), (III') or (IV), wherein the citric acid ester is a citric acid ester of mono and diglycerides of fatty acids (E472c).

The emulsifier system of the embodiment of the present invention can also comprise other emulsifier(s) (=co-emulsifiers). In case such one or more co-emulsifers are used, the emulsifier system should still crystallise before the core crystallises.

Suitable co-emulsifiers are i.e. polysorbates (polysorbates are oily liquids derived from PEG-ylated sorbitan (a derivative of sorbitol) esterified with fatty acids), such as Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate);

Phospholipids, such as phosphatidic acid (phosphatidate), phosphatidylethanolamine (cephalin). phosphatidylcholine (lecithin), hydrogenated lecithin, phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin) and ceramide phosphorylglycerol; and stearoyl-2-lactylate such as sodium-stearoyl-2-lactylate (E 481).

Therefore the present invention also relates to solid lipid nanoparticles (VI), which are solid lipid nanoparticles (I), (II), (III), (III'), (IV) or (V), wherein the emulsifier system comprises at least one co-emulsifier.

Therefore the present invention also relates to solid lipid nanoparticles (VI'), which are solid lipid nanoparticles (I), (II), (III), (III'), (IV), (V) or (VI), wherein the emulsifier system comprises at least one co-emulsifier chosen from the group consisting of polysorbates, phospholipids and stearoyl-2-lactylate.

Therefore the present invention also relates to solid lipid nanoparticles (VI''), which are solid lipid nanoparticles (I), (II), (III), (III'), (IV), (V), (VI) or (VI'), wherein the emulsifier system comprises at least one co-emulsifier chosen from the group consisting of Polysorbate 40 (polyoxyethylene (20) sorbitan monopalmitate), Polysorbate 60 (polyoxyethylene (20) sorbitan monostearate), Polysorbate 80 (polyoxyethylene (20) sorbitan monooleate), phosphatidic acid (phosphatidate), phosphatidylethanolamine (cephalin). phosphatidylcholine (lecithin), hydrogenated lecithin, phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin), ceramide phosphorylglycerol and stearoyl-2-lactylate.

Therefore the present invention also relates to solid lipid nanoparticles (VI'''), which are solid lipid nanoparticles (I), (II), (III), (III'), (IV), (V), (VI) or (VI'), wherein the emulsifier system comprises at least one co-emulsifier chosen from the group consisting of lecithin, hydrogenated lecithin and sodium-stearoyl-2-lactylate (E 481).

The concentration of the at least one citric acid ester is 0.1-30 weight-% (wt-%), based on the total weight of the SLN, preferably 0.5-20 wt-%.

Therefore the present invention also relates to solid lipid nanoparticles (VII), which are solid lipid nanoparticles (I), (II), (III), (III'), (IV), (V), (VI), (VI'), (VI'') or (VI'''), wherein the concentration of the at least one citric acid ester is 0.1-30 weight-% (wt-%), based on the total weight of the SLN.

Therefore the present invention also relates to solid lipid nanoparticles (VII'), which are solid lipid nanoparticles (I), (II), (III), (III'), (IV), (V), (VI), (VI'), (VI'') or (VI'''), wherein the concentration of the at least one citric acid ester is 0.5-20 wt-%.

The concentration of the at least co-emulsifier is 0.1-30 wt-%, based on the total weight of the SLN, preferably 0.5-20 wt-%.

Therefore the present invention also relates to solid lipid nanoparticles (VIII), which are solid lipid nanoparticles (I), (II), (III), (III'), (IV), (V), (VI), (VI'), (VI''); (VI'''), (VII) or (VII'), wherein the concentration of the at least co-emulsifier is 0.1-30 wt-%, based on the total weight of the SLN.

Therefore the present invention also relates to solid lipid nanoparticles (VIII'), which are solid lipid nanoparticles (I), (II), (III), (III'), (IV), (V), (VI), (VI'), (VI''); (VI'''), (VII) or (VII'), wherein the concentration of the at least co-emulsifier is 0.5-20 wt-%.

The concentration of the lipophilic and/or amphiphilic active ingredient can be up to 60 wt-%, based on the total amount of the SLN.

Therefore the present invention also relates to solid lipid nanoparticles (IX), which are solid lipid nanoparticles (I), (II), (III), (III'), (IV), (V), (VI), (VI'), (VI''); (VI'''), (VII), (VII'), (VIII) or (VIII'), wherein the concentration of the lipophilic and/or amphiphilic active ingredient is up to 60 wt-%, based on the total amount of the SLN.

The SLN can be prepared according to methods known from the prior art. For example preparation methods at elevated temperatures (above the melting temperature of the lipid) such as hot homogenization and hot microemulsification, and there are methods at room temperature or below (i.e. below the melt temperature of the lipids), such as milling techniques (Kakran, et al., 2012; R. H. Müller, Gohla, & Keck, 2011; Rainer H. Müller, et al., 2000).

Preferably SLNs according to the present invention are produced by using hot homogenisation.

Therefore the present invention also relates to a process of production of solid lipid nanoparticles (IX), which are solid lipid nanoparticles (I), (II), (III), (III'), (IV), (V), (VI), (VI'), (VI''); (VI'''), (VII), (VII'), (VIII), (VIII') or (IX), characterised in that the process is a hot homogenisation process.

The SLNs according to the present invention can be used in various fields of application. The field of application usually depends on the lipophilic and/or amphiphilic active ingredient, which are incorporated.

The SLNs can be used as such or they can be used for the production of food products, feed products or personal care products.

Therefore, a further embodiment of the present invention relates to the use of the solid lipid nanoparticles (I), (II), (III), (III'), (IV), (V), (VI), (VI'), (VI''); (VI'''), (VII), (VII'), (VIII), (VIII') or (IX) in the production of food products, feed products or personal care products.

The amount of SLN (and the lipophilic and/or amphiphilic active ingredients) in such products depends on the kind of product and the lipophilic and/or amphiphilic active ingredients.

Furthermore the present invention also relates to of food products, feed products and personal care products comprising solid lipid nanoparticles (I), (II), (III), (III'), (IV), (V), (VI), (VI'), (VI''); (VI'''), (VII), (VII'), (VIII), (VIII') or (IX).

The invention is illustrated by the following Examples. All temperatures are given in ° C. and all parts and percentages are related to the weight.

EXAMPLE 1

0.6 wt-% of Citric Acid Ester Solution

A 50 g sample weight, of this example consists of 90 wt-% surfactant (Citric acid ester E472c, 0.6 wt-%)/sodium phosphate buffer solution (10 mM, pH=7) and 10 wt-% glyceryl tripalmitate. The glyceryl tripalmitate was heated to 85° C. to fully melt the lipid. After heating separately the surfactant buffer solution at the same temperature (85° C.), the lipid melt and the surfactant aqueous phase were mixed together and stirred for one minute by using a homogenizer standard unit (Labworld-online, Staufen, Germany). The content of E472c was 0.54 wt-%, based on the total weight of the sample. The so-formed hot premix was directly homogenized by passing the emulsion 5 times at 10.000 psi (≈700 bar) through a high pressure homogenizer (EmulsiFlex-C3, Avestin Inc., Ottawa, Canada). Prior to homogenization the high-pressure homogenizer was heated up by cycling 5 times boiling water through the machine, to prevent emulsion crystallization. During homogenization the already homogenized sample was collected in a flask, which was located in a water-bath. The fine emulsion was then divided in two parts, which were stored in an ice bath for one hour to induce fat crystallization. Afterwards, the two dispersion portions were stored at 7, or 25° C., respectively.

EXAMPLE 2

2.4 wt-% Phosphatidylcholine with 3.6 wt-% Citric Acid Ester, Solution

Example 2 done in analogy to Example 1 with the exception that the surfactant solution contains a mixture of high melting Phosphatidylcholine and citric acid ester in a 1:1.5 ratio, respectively. The content of the total amount of surfactant being 5.4 wt-% (being the one of citric acid ester 3.24 wt-% and of Phosphatidylcholine 2.16 wt-%) based on the total weight of the sample.

Storage Stabilities of Example 1 and 2

The physical stability of the samples described in example 1 and 2 was measured over a period of 3 weeks (at 7° C.).

After 3 weeks of storage, the samples were still homogenous and fluid. No gelation, aggregation, or sedimentation was observed.

The invention claimed is:
1. Solid lipid nanoparticles comprising a mixture of:
  (a) a lipid phase core which comprises:
    (i) a lipid phase in a solid state, wherein the lipid phase is at least one oil selected from the group consisting of triglycerides, partial glycerides, fatty acids, steroids and waxes; and
    (ii) optionally at least one lipophilic and/or amphiphilic active ingredient, and
  (b) an emulsifier system which comprises at least one citric acid ester emulsifier selected from the group consisting of citric acid esters of mono-glycerides and di-glycerides of fatty acids.
2. The solid lipid nanoparticles according to claim 1, wherein the emulsifier system has a crystallization point which is lower than a crystallization point of the core.
3. The solid lipid nanoparticles according to claim 1, wherein the lipophilic and/or amphiphilic active ingredient is selected from the group consisting of antimicrobials, antioxidants, polyphenols, vitamins, polyunsaturated fatty acids (PUFAs) and dyestuffs.
4. The solid lipid nanoparticles according to claim 1, wherein the emulsifier system comprises at least one co-emulsifier.
5. The solid lipid nanoparticles to claim 4, wherein the co-emulsifier is selected from the group consisting of polysorbates, phospholipids and stearoyl-2-lactylat.
6. The solid lipid nanoparticles according to claim 1 wherein the at least one citric acid ester emulsifier is present in an amount of 0.1-30 wt-% based on the total weight of the solid lipid nanoparticles.
7. The solid lipid nanoparticles according to claim 4, wherein the at least co-emulsifier is present in an amount of 0.1-30 wt-% based on the total weight of the solid lipid nanoparticles.
8. The solid lipid nanoparticles to claim 1, wherein the lipophilic and/or amphiphilic active ingredient is present in an amount up to 60 wt-%, based on the total amount of the solid lipid nanoparticles.
9. The solid lipid nanoparticles according to claim 4, wherein each of the at least one citric acid ester emulsifier and the at least one co-emulsifier is present in an amount of 0.5-20 wt-%, based on the total weight of the solid lipid nanoparticles.
10. Food products, feed products and personal care products comprising the solid lipid nanoparticles as claimed in claim 1.

* * * * *